(12) United States Patent
Gallagher

(10) Patent No.: US 6,880,699 B2
(45) Date of Patent: Apr. 19, 2005

(54) CARTRIDGE FOR HOLDING ASYMMETRIC SURGICAL CLIPS

(75) Inventor: Richard J. Gallagher, Raleigh, NC (US)

(73) Assignee: Pilling Weck Incorporated, Limerick, PA (US)

( * ) Notice: Subject to any disclaimer, the term of this patent is extended or adjusted under 35 U.S.C. 154(b) by 0 days.

(21) Appl. No.: 10/229,240

(22) Filed: Aug. 27, 2002

(65) Prior Publication Data

US 2004/0040875 A1 Mar. 4, 2004

(51) Int. Cl.[7] .......................... B65D 85/24; B65D 83/10
(52) U.S. Cl. ...................... 206/339; 206/340; 206/363
(58) Field of Search .................... 206/338–341, 206/63.3, 438, 477, 478, 561, 560, 363, 370; 606/157, 158; 227/902

(56) References Cited

U.S. PATENT DOCUMENTS

| | | | | |
|---|---|---|---|---|
| 3,270,745 | A | 9/1966 | Wood | 128/325 |
| 3,326,216 | A | 6/1967 | Wood | 128/325 |
| 3,363,628 | A | 1/1968 | Wood | 128/325 |
| 3,439,522 | A | 4/1969 | Wood | 72/410 |
| 3,439,523 | A | 4/1969 | Wood | 72/410 |
| 3,713,533 | A | 1/1973 | Reimels | 206/56 |
| 4,076,120 | A | 2/1978 | Carroll et al. | 206/339 |
| 4,146,130 | A | 3/1979 | Samuels et al. | 206/340 |
| 4,294,355 | A | 10/1981 | Jewusiak et al. | 206/339 |
| 4,361,229 | A | 11/1982 | Mericle | 206/339 |
| 4,509,518 | A | 4/1985 | McGarry et al. | 128/325 |
| 4,696,396 | A | 9/1987 | Samuels | 206/339 |
| 4,834,096 | A | 5/1989 | Oh et al. | 128/325 |
| 4,936,447 | A | * 6/1990 | Peiffer | 206/339 |
| 4,971,198 | A | 11/1990 | Mericle | 206/339 |
| 5,046,611 | A | 9/1991 | Oh | 206/339 |
| 5,062,846 | A | 11/1991 | Oh et al. | 606/158 |
| 5,100,416 | A | 3/1992 | Oh et al. | 606/139 |
| 5,201,416 | A | 4/1993 | Taylor | 206/339 |
| 5,509,920 | A | 4/1996 | Phillips et al. | 606/157 |
| 6,419,682 | B1 | * 7/2002 | Appleby et al. | 206/339 |

* cited by examiner

*Primary Examiner*—Mickey Yu
*Assistant Examiner*—J. Gregory Pickett
(74) *Attorney, Agent, or Firm*—Jenkins, Wilson & Taylor, P.A.

(57) ABSTRACT

A cartridge is provided for retaining surgical clips, and particularly clips used in surgical ligating procedures that have an asymmetrical profile. The cartridge comprises a base having a base longitudinal axis. A plurality of axially spaced walls extend from the base and are transversely disposed in relation to the base axis. The walls define a plurality of axially spaced compartments therebetween. Each wall has a central wall axis that is generally perpendicular to the base axis. The cartridge further comprises a plurality of clip support members. Each clip support member is disposed within a respective compartment and comprises an asymmetrically shaped cross-section in relation to the central wall axis.

10 Claims, 16 Drawing Sheets

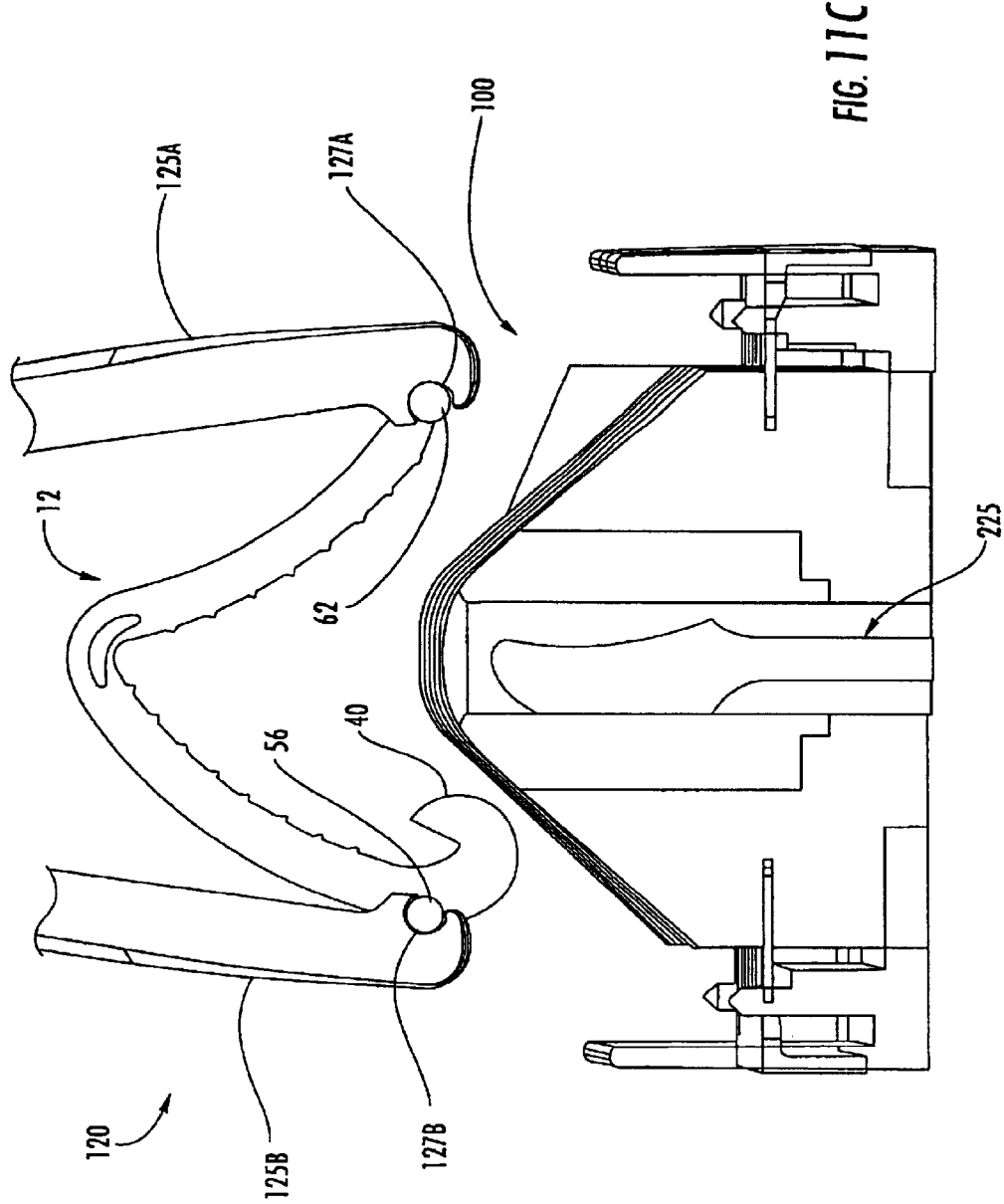

CARTRIDGE FOR HOLDING ASYMMETRIC SURGICAL CLIPS

TECHNICAL FIELD

The present invention generally relates to the storage and subsequent extraction of clips, and particularly surgical ligating clips characterized by an asymmetric design, in preparation for use of the clips in an appropriate procedure such as hemostasis. More particularly, the present invention relates to a clip cartridge adapted for retaining asymmetric clips in an improved manner and for facilitating the loading of such a clip into a clip manipulating instrument for subsequent extraction of the clip from the clip cartridge while loaded in the clip manipulating instrument.

BACKGROUND ART

Many surgical procedures require vessels or other tissues of the human body to be ligated during the surgical process. For example, many surgical procedures require cutting blood vessels (e.g., veins or arteries), and these blood vessels may require ligation to reduce bleeding. In some instances, a surgeon may wish to ligate the vessel temporarily to reduce blood flow to the surgical site during the surgical procedure. In other instances a surgeon may wish to permanently ligate a vessel. Ligation of vessels or other tissues can be performed by closing the vessel with a ligating clip, or by suturing the vessel with surgical thread. The use of surgical thread for ligation requires complex manipulations of the needle and suture material to form the knots required to secure the vessel. Such complex manipulations are time-consuming and difficult to perform, particularly in endoscopic surgical procedures, which are characterized by limited space and visibility. By contrast, ligating clips are relatively easy and quick to apply. Accordingly, the use of ligating clips in endoscopic as well as open surgical procedures has grown dramatically.

Various types of hemostatic and aneurysm clips are used in surgery for ligating blood vessels or other tissues to stop the flow of blood. Such clips have also been used for interrupting or occluding ducts and vessels in particular surgeries such as sterilization procedures. Typically, a clip is applied to the vessel or other tissue by using a dedicated mechanical instrument commonly referred to as a surgical clip applier, ligating clip applier, or hemostatic clip applier. Generally, the clip is left in place after application to the tissue until hemostasis or occlusion occurs. At some point thereafter, the clip is removed by using a separate instrument dedicated for that purpose, i.e., a clip removal instrument.

Ligating clips can be classified according to their geometric configuration (e.g., symmetric clips or asymmetric clips), and according to the material from which they are manufactured (e.g., metal clips or polymeric clips). Symmetric clips are generally "U" or "V" shaped and thus are substantially symmetrical about a central, longitudinal axis extending between the legs of the clip. Symmetric clips are usually constructed from metals such as stainless steel, titanium, tantalum, or alloys thereof. By means of a dedicated clip applier, the metal clip is permanently deformed over the vessel. An example of one such clip is disclosed in U.S. Pat. No. 5,509,920 to Phillips et al. An example of a metallic clip applier is disclosed in U.S. Pat. No. 3,326,216 to Wood, in which a forceps-type applier having conformal jaws is used to grip and maintain alignment of the clip during deformation. Such appliers may additionally dispense a plurality of clips for sequential application, as disclosed in U.S. Pat. No. 4,509,518 to McGarry et al.

With the advent of high technology diagnostic techniques using computer tomography (CATSCAN) and magnetic resonance imaging (MRI), metallic clips have been found to interfere with the imaging techniques. To overcome such interference limitations, biocompatible polymers have been increasingly used for surgical clips. Unlike metallic clips, which are usually symmetric, polymeric clips are usually asymmetric in design and hence lack an axis of symmetry. Inasmuch as the plastic clip cannot be permanently deformed for secure closure around a vessel or other tissue, latching mechanisms have been incorporated into the clip design to establish closure conditions and to secure against re-opening of the vessel. For example, polymeric clips are disclosed in U.S. Pat. No. 4,834,096 to Oh et al. and U.S. Pat. No. 5,062,846 to Oh et al., both of which are assigned to the assignee of the present invention. These plastic clips generally comprise a pair of curved legs joined at their proximal ends with an integral hinge or heel. The distal ends of the curved legs include interlocking latching members. For example, the distal end of one leg terminates in a lip or hook structure into which the distal end of the other leg securely fits to lock the clip in place. The distal ends of the clips taught by Oh et al. also include lateral bosses that are engaged by the jaws of the clip applier. A clip applier specifically designed for asymmetric plastic clips is used to close the clip around the tissue to be ligated, and to latch or lock the clip in the closed condition. In operation, the jaws of this clip applier are actuated into compressing contact with the legs of the clip. This causes the legs to pivot inwardly about the hinge, thereby deflecting the hook of the one leg to allow reception therein of the distal end of the other leg. A clip applier designed for use with asymmetric plastic clips in an open (i.e., non-endoscopic) surgical procedure is disclosed in U.S. Pat. No. 5,100,416 to Oh et al., assigned to the assignee of the present invention.

In addition to compatibility with sophisticated diagnostic techniques, asymmetric clips have other advantages over symmetric clips. For example, because asymmetric clips are formed from polymeric materials, the mouths of asymmetric clips can be opened wider than the mouths of symmetric clips. This allows a surgeon to position the clip about the desired vessel with greater accuracy. In addition, a clip of the type described in U.S. Pat. Nos. 4,834,096 and 5,062,846 can be repositioned before locking the clip on the vessel or before removing the clip from the vessel, in a process referred to as "approximating" the clip.

Because clips of the type just described are small and several clips are often used in a surgical procedure, holding devices are employed to store and retain the clips between the time of their manufacture and/or packaging and ultimate use in a surgical procedure. Numerous clip cartridges have been developed, some of which strive to prevent the clips from becoming unduly loosened or even completely dislodged during shipment and handling. A distinction can be made between clip cartridges intended for use with "manual" clip appliers and those intended for use with "automatic" clip appliers. As used herein, the term "automatic" denotes the kind of clip appliers that retain a plurality of hemostatic clips adjacent to the jaws of a clip applier in a way such that a new clip is automatically fed to the jaws after the previous clip has been crimped into place. By contrast, the term "manual" denotes the kind of clip appliers that receive one clip at a time between the jaws, and which have to be reloaded manually after the previous clip has been crimped. These manual instruments usually have a forceps-type design The reloading operation is generally accomplished by inserting the jaws of the applier into a clip holder or cartridge and engaging or grasping a clip contained therein. Many types of clip cartridges currently available contain a plurality of longitudinally spaced clip retaining chambers. A single clip is retained in each chamber by a variety of means, and is removed from its chamber by a forceps-type clip applier that is inserted into the selected clip chamber and secured to the clip sufficiently to overcome whatever clip retention means is utilized, thereby enabling the clip to be removed from the clip chamber.

Various mechanisms are known by which clips may be retained within the chambers of clip cartridges. With respect to metallic clips, friction between the clip and the side walls of its individual chamber is often sufficient to retain the clip. The clip cartridges are generally made of molded plastic material, such that the walls of each clip chamber are somewhat resilient and able to be pushed away from each other when the clip applier jaws are inserted into the chamber to retrieve the clip. An example of a cartridge holding the clips in their respective clip chambers by means of frictional engagement with the side walls of each chamber is shown in U.S. Pat. No. 4,076,120 to Carroll et al. In some prior art clip cartridges designed for metallic clips, each individual clip chamber is provided with a central post generally conforming to the shape of the open clip although being slightly larger so that when the clip is pushed onto the central post, frictional contact between the legs of the clip and the central post retains the clip within its chamber. Cartridges of this type are shown in U.S. Pat. Nos. 3,270,745; 3,326,216; 3,363,628; 3,439,522; and 3,439,523, all issued to Wood.

Prior art cartridges are also known that retain clips in a partially straightened state by maintaining each clip under tension within its chamber, through the interaction between the central post in the chamber and the central part of the clip and protrusions extending into each chamber toward the central post (from the ends). The clip is retained by having its central hinge part pushed upwardly by the central post and its ends pushed downwardly by the protrusions. Such a cartridge is shown in U.S. Pat. No. 3,713,533 to Reimels and U.S. Pat. No. 4,146,130 to Samuels et al.

U.S. Pat. No. 4,696,396 to Samuels discloses another type of cartridge that has a plurality of ribs extending from each side wall of each clip chamber inwardly toward the clip to retain the clip by frictional engagement with the ribs. The aforementioned U.S. Pat. No. 4,146,130 to Samuels et al. shows an alternative embodiment for the situation where clips are intended to be loosely maintained in the cartridge without frictional engagement between the clips and the chamber, the clips in such an event being retained in each cartridge by a covering tape which may be easily severed by the applier as desired.

Cartridges suitable for holding metallic clips are generally not suitable for likewise holding polymeric clips, in large part because polymeric clips inherently have a greater resiliency and typically have a non-symmetrical structure. For example, the aforementioned prior art cartridges that rely on the interaction between the clip and central post are not suitable for use with non-metallic clips because there is insufficient compression in non-metallic clips to cause them to grip the center post adequately. Likewise, frictional engagement with either the side and/or end walls of the chamber could possibly, over a long period of storage time, adversely affect performance of the clips. It would therefore be preferable to retain non-metallic clips in a natural, relaxed state without any external stress applied to the clips until they are ready for use.

One known prior art method of holding plastic clips is disclosed in U.S. Pat. No. 4,294,355 to Jewusiak et al., which discloses one or more resilient fingers associated with each clip chamber for holding each clip in a particular fixed orientation. The entire cartridge can be covered by a thin film having a plurality of lines of weakness over each clip to identify the clip location for easy retrieval by the clip applier. Each clip is supported on a post formed by a sharply pointed tip between straight edges. Such a post is essentially a pivot point on which the clip is excessively free to move and is unbalanced, and thus makes difficult the loading of the clip into the jaws of an applier inserted into the cartridge.

U.S. Pat. No. 4,361,229 to Mericle discloses a cartridge for non-metallic clips wherein each clip is retained in its individual chamber by the interaction between a central post supporting each clip and paper flaps extending into each end of each chamber, the paper flaps being formed from a paper film interposed between a base portion of the cartridge (to which the central post is secured) and a top portion. The central posts present narrow cross-sections with sharp tips, and thus act as undesirable pivot points rather than supports for asymmetric clips.

Similar to U.S. Pat. Nos. 4,294,355 and 4,361,229, U.S. Pat. No. 5,046,611 to Oh and U.S. Pat. No. 5,201,046 to Taylor disclose clip cartridges in which each post is defined by a pointed tip between straight edges. As in the previous cases, these types of posts act more as pivots than supports for clips, and thus do not provide optimal support for asymmetric clips.

In view of the foregoing discussion of representative prior art, it would be advantageous to provide an improved clip cartridge for retaining clips, and especially asymmetric clips, in a manner suitable for shipping and handling and in preparation for extraction of the clips from the clip cartridge by a clip applying instrument.

DISCLOSURE OF THE INVENTION

According to one embodiment of the present invention, a cartridge for retaining clips comprises a base having a base longitudinal axis, a plurality of axially spaced walls extending from the base, and a plurality of clip support members. The walls are transversely disposed in relation to the base axis. The walls define a plurality of axially spaced compartments therebetween. Each wall has a central wall axis that is generally perpendicular to the base axis. Each clip support member is disposed within a respective compartment, and comprises an arcuate surface and an asymmetrically shaped cross-section in relation to the central wall axis.

According to another embodiment of the present invention, each clip support member comprises a concave support edge, a convex support edge, and a rounded support edge joining the concave support edge and the convex support edge. Preferably, each rounded support edge is disposed in an offset relation to the central wall axis.

According to yet another embodiment of the present invention, a cartridge for retaining clips comprises a base having a base longitudinal axis, a plurality of axially spaced walls extending from the base, a plurality of asymmetric clip support members, and a clip retainer supported by the base. The walls are transversely disposed in relation to the base axis, and define a plurality of axially spaced compartments therebetween. Each compartment comprises a first lateral opening defined on a first side of the base axis, and a second lateral opening defined on a second side of the base axis in opposing relation to the first lateral opening. Each clip support member is disposed within a respective compartment above the base. The clip retainer comprises a plurality of opposing pairs of first and second resilient tabs. Each first tab extends into a corresponding compartment through its corresponding first lateral opening. Each second tab extends into the corresponding compartment through its corresponding second lateral opening.

According to still another embodiment of the present invention, each first and second tab of the clip retainer terminates at an inside tab edge, and each inside tab edge comprises a tab recess.

According to an additional aspect of the present invention, a method is provided for loading an asymmetric clip into a clip applier. Preferably, the clip is of the type that comprises a first leg, a second leg, and a hinge region joining the first and second legs. In addition, a distal end of the first leg comprises a first boss and a distal end of the second leg comprises a second boss. The clip applier is preferably of the type that comprises a pair of opposing first and second jaws, with the first jaw comprising a first jaw recess and the second jaw comprising a second jaw recess. According to the method, a clip cartridge is provided. The clip cartridge comprises a plurality of compartments and a plurality of clip support members. Each clip support member is disposed in a corresponding compartment and comprises an asymmetric cross-section. At least one clip is loaded in at least one of the compartments. The clip applier is inserted into the compartment, with the first jaw adjacent to the first leg of the clip and the second jaw adjacent to the second leg of the clip. The first boss of the first leg moves into locking engagement with the first jaw recess and the second boss of the second leg moves into locking engagement with the second jaw recess. At this point, the first and second jaws of the clip applier can be removed from the compartment with the clip retained by the first and second jaws, thereby extracting the clip from the clip cartridge.

It is therefore an object of the present invention to provide a clip cartridge for retaining clips during shipping and handling while enabling the withdrawal of the clips by a clip applier in preparation for use such as a surgical procedure.

It is another object of the present invention to provide such a clip cartridge that is adapted for retaining clips of asymmetric design.

It is another object of the present invention to provide such a clip cartridge that is adapted for polymeric retaining clips of asymmetric design.

It is a further object of the present invention to provide a clip cartridge adapted to retain clips in an improved manner, whereby movement of the clips on their respective clip supports within the clip cartridge is restricted so as to facilitate engagement of the clip by a clip applier inserted into the clip cartridge.

It is a further object of the present invention to provide a clip cartridge in which a plurality of individual clip compartments are formed and include a corresponding plurality of asymmetrically shaped clip supporting elements.

Some of the objects of the invention having been stated hereinabove, other objects will become evident as the description proceeds when taken in connection with the accompanying drawings as best described hereinbelow.

BRIEF DESCRIPTION OF THE DRAWINGS

FIG. 11C is cross-sectional view of the clip cartridge showing the clip being extracted from the compartment of the clip cartridge.

DETAILED DESCRIPTION OF THE INVENTION

Figure 1A:
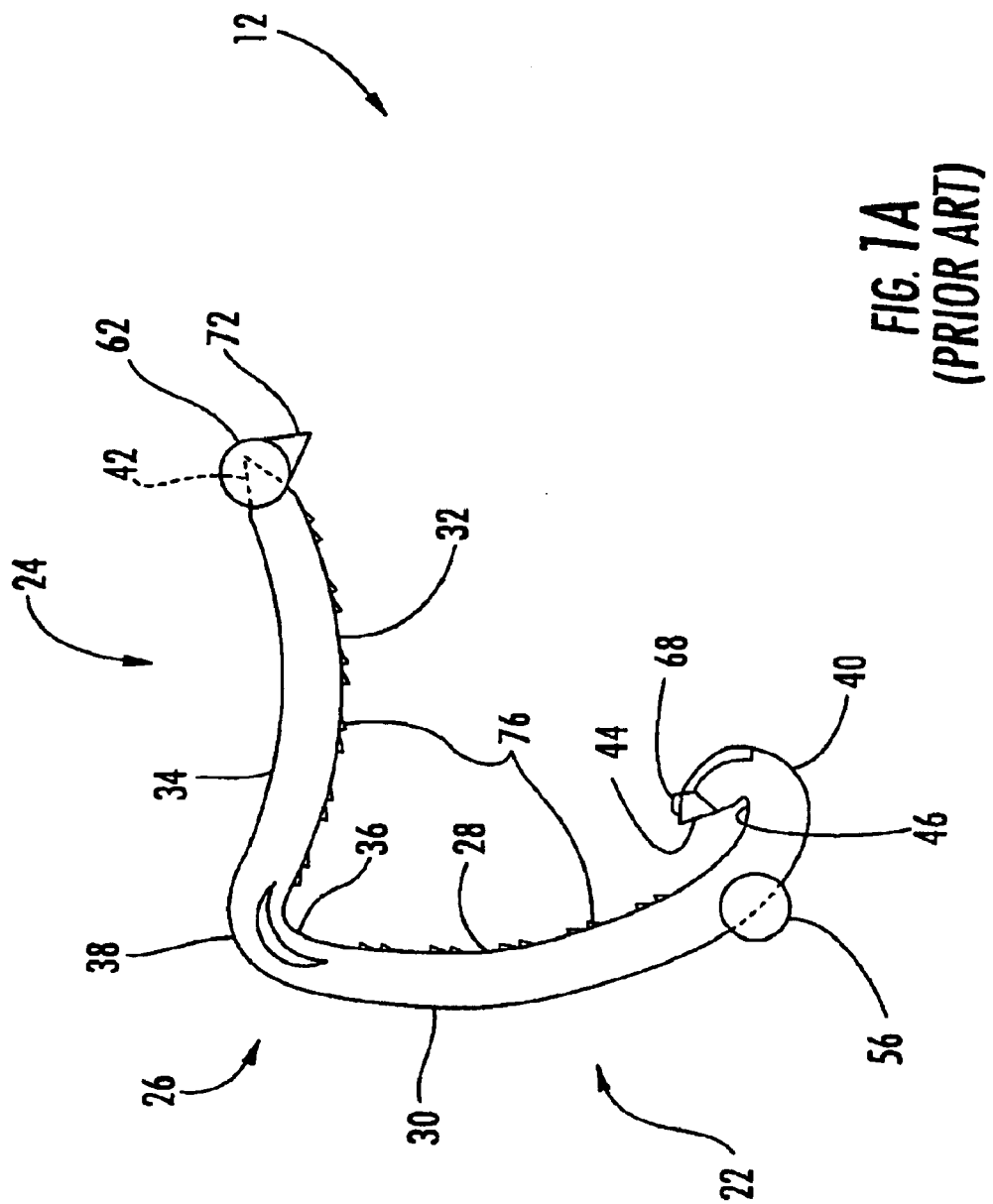
FIG. 1A is a side elevation view of one example of an asymmetric clip suitable for use in conjunction with the clip cartridge of the present invention.
Figure 1B:
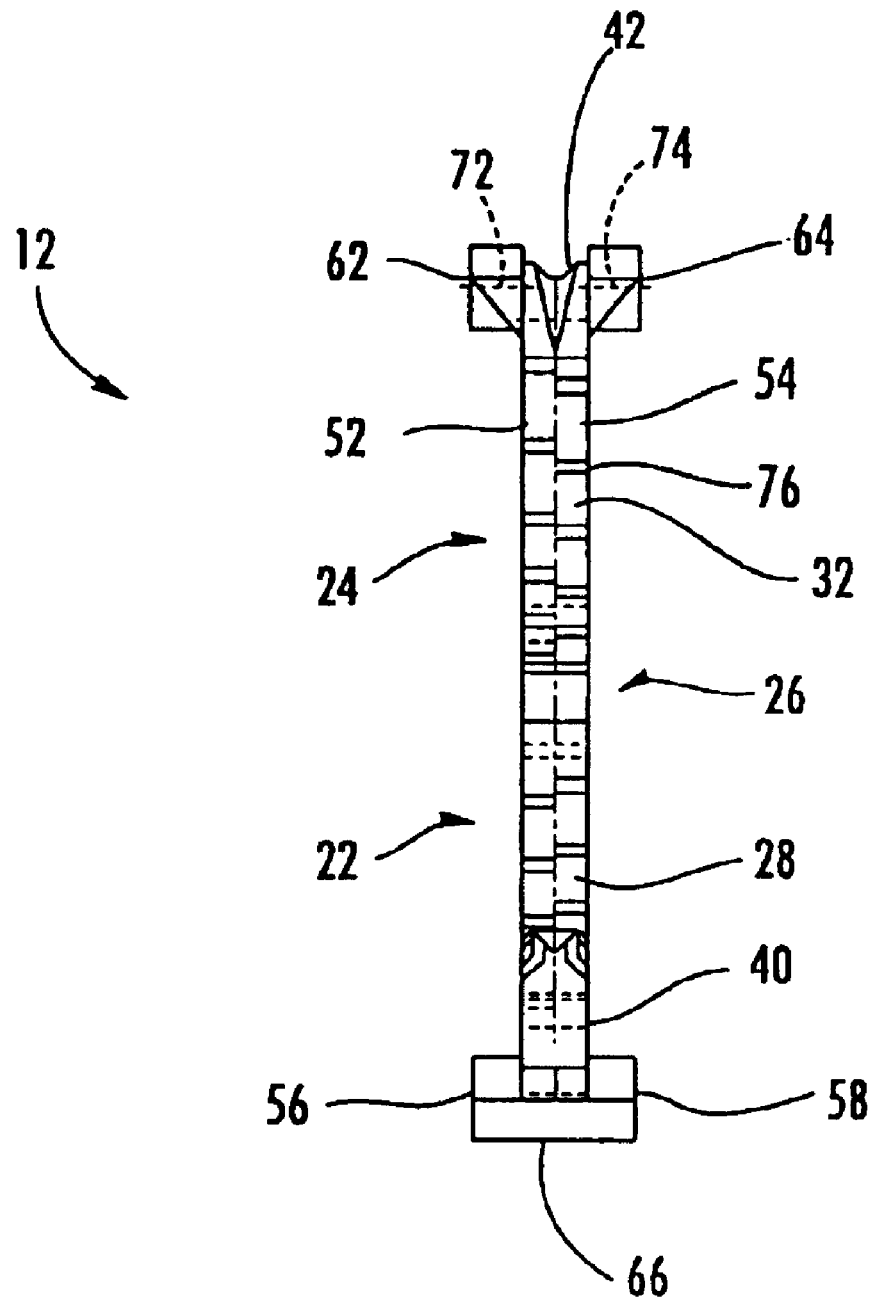
FIG. 1B is a front elevation view of the clip illustrated in FIG. 1A directed into the open side of the clip.

Referring now to FIGS. 1A and 1B, one example is illustrated of an asymmetric surgical clip, generally designated 12, that is suitable for use in conjunction with the present invention. This clip 12 and others of similar design are particularly useful as hemostatic clips that can be latched around a vessel or other type of tissue to ligate the vessel and thereby stop or reduce the flow of fluid through the vessel. Clip 12 can be constructed from any suitable biocompatible material, such as certain metals and polymers. The present invention is particularly suitable for practice with polymeric clips. Thus, clip 12 preferably comprises a one-piece integral polymeric body formed from a suitable strong biocompatible engineering plastic such as the type commonly used for surgical implants. Examples include polyethylene terephthalate (PET), polybutylene terephthalate (PBT), polyoxymethylene, or other thermoplastic materials having similar properties that can be injection-molded, extruded or otherwise processed into like articles.

The body of clip 12 comprises a first or outer leg, generally designated 22, and a second or inner leg, generally designated 24. First and second legs 22 and 24 are joined at their proximal ends by an integral hinge section, generally designated 26. First and second legs 22 and 24 have complementary arcuate profiles. Thus, first leg 22 has a concave inner surface 28 and a convex outer surface 30, and second leg 24 has a convex inner surface 32 and a concave outer surface 34. Convex inner surface 32 of second leg 24 and concave inner surface 28 of first leg 22 have substantially matching radii of curvature. Hinge section 26 has a continuous concave inner surface 36 and a continuous convex outer surface 38. Concave inner surface 36 of hinge section 26 joins concave inner surface 28 of first leg 22 and convex inner surface 32 of second leg 24. Convex outer surface 38 of hinge section 26 joins convex outer surface 30 of first leg 22 and concave outer surface 34 of second leg 24. First leg 22 transitions to a curved, C-shaped hook section 40 at its distal end. Second leg 24 transitions to a pointed tip section 42 at its distal end. Hook section 40 is distally reversely curved inwardly, and has a transverse beveled surface 44. Beveled surface 44 and concave inner surface 28 define a latching recess 46, which is adapted for conformally engaging tip section 42 in the course of compressing clip 12 into a latched or locked position around a vessel or other tissue.

As best shown in FIG. 1B, which is an elevation view directed into the open concave side of clip 12, clip 12 comprises parallel, opposed side surfaces 52 and 54. Typically, the body of clip 12 has a constant thickness between side surfaces 52 and 54. Adjacent to the distal end of the first leg 22 and immediately inwardly of hook section 40, a pair of cylindrical bosses 56 and 58 are formed coaxially on the opposed lateral surfaces of first leg 22. In the illustrated example of clip 12, a bridge section 66 couples bosses 56 and 58 together. As evident in FIG. 1A, bosses 56 and 58 project outwardly beyond convex outer surface 30 of first leg 22. Referring back to FIG. 1B, at the distal end of inner leg 24, another pair of cylindrical bosses 62 and 64 are formed coaxially on the opposed lateral surfaces of inner leg 24 at tip section 42. As evident in FIG. 1A, bosses 62 and 64 of second leg 24 extend longitudinally forwardly beyond tip section 42. Also in the illustrated example of clip 12, hook section 40 of first leg 22 terminates at a sharp tip 68, the distal end of second leg 24 includes a pair of sharp tissue-penetrating teeth 72 and 74, and both first and second legs 22 and 24 have a plurality of protrusions or teeth 76 extending from their respective inner surfaces 28 and 32. These latter features are designed to engage the tissue of the vessel being clamped and assist in preventing the vessel from sliding laterally or longitudinally during or following clip closure. It will be noted, however, that other clips equally suitable for use in conjunction with the invention do not contain such features.

In the practice of ligating a vessel as understood by persons skilled in the art, clip 12 is designed to be compressed into a latched or locked position around the vessel through the use of an appropriate clip applicator instrument, such as the type described in the aforementioned U.S. Pat. No. 5,100,416. The clip applicator instrument engages bosses 56, 58, 62 and 64 of clip 12 and pivots bosses 56, 58, 62 and 64 inwardly about hinge section 26. This causes first and second legs 22 and 24 to close around the vessel, with convex inner surface 32 of second leg 24 and complementary concave inner surface 28 of first leg 22 contacting the outer wall of the vessel. Tip section 42 of second leg 24 then begins to contact hook section 40. Further pivotal movement by the applicator instrument longitudinally elongates first leg 22 and deflects hook section 40, allowing tip section 42 to align with latching recess 46. Upon release of the applicator instrument, tip section 42 snaps into and is conformably seated in latching recess 46, at which point clip 12 is in its latched condition. In the latched condition, tip section 42 is engaged between concave inner surface 28 and beveled surface 44, thereby securely clamping a designated vessel or other tissue between concave inner surface 28 and convex inner surface 32.

Clips similar to clip 12 are described in detail in commonly assigned U.S. Pat. No. 4,834,096 to Oh et al. and 5,062,846 to Oh et al., the disclosures of which are incorporated herein in their entireties. In addition, a particularly suitable clip is the HEM-O-LOK® clip commercially available from the assignee of the present invention. These clips are currently available in sizes designated "M", "ML", and "L". The clip cartridge of the invention described hereinbelow can be adapted to accommodate any sizes of HEM-O-LOK® clips commercially available.

Figure 2A:
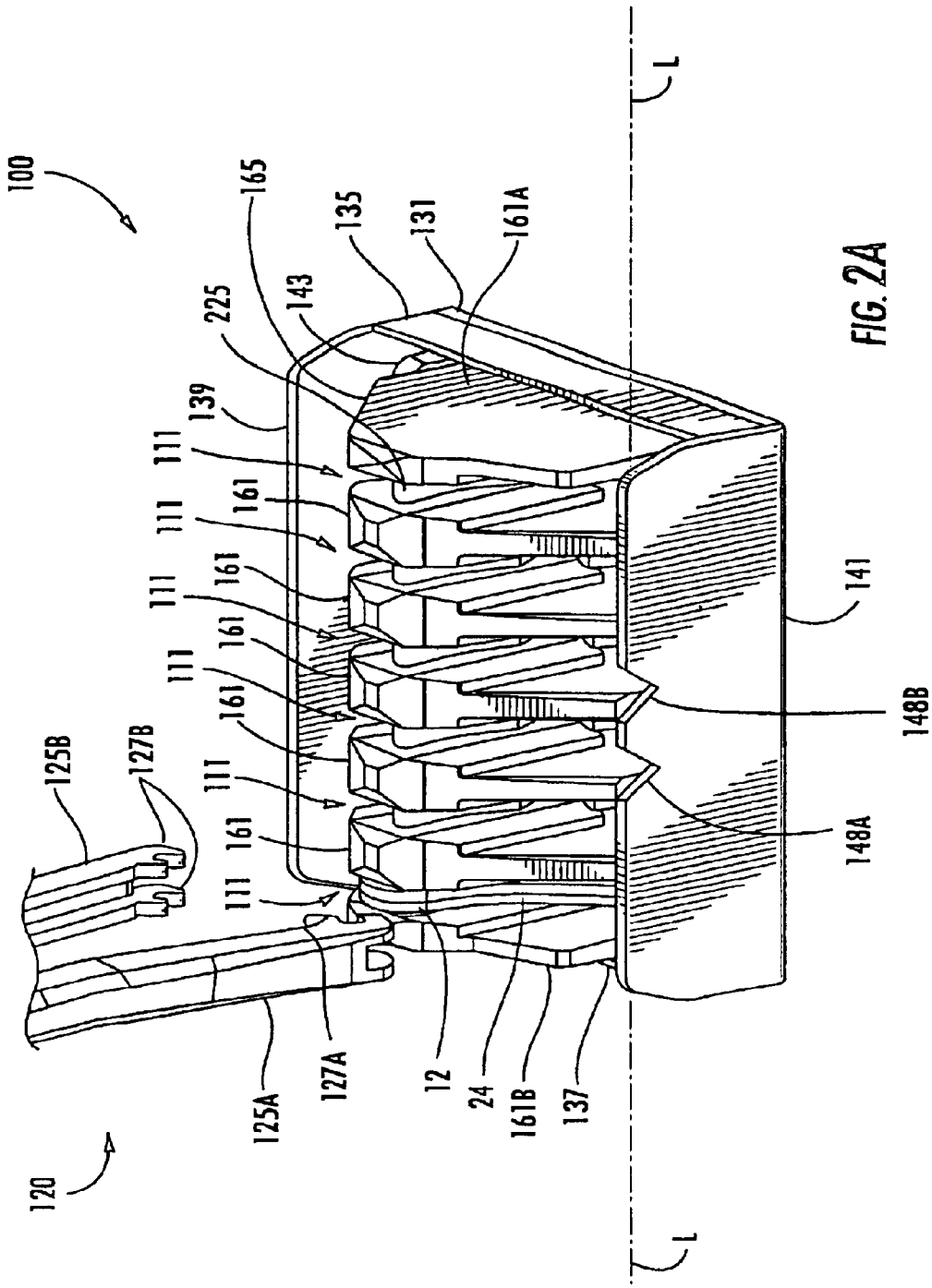
FIG. 2A is a perspective view of a clip cartridge provided in accordance with the present invention, showing a clip applier being inserted into a compartment thereof.
Figure 2B:
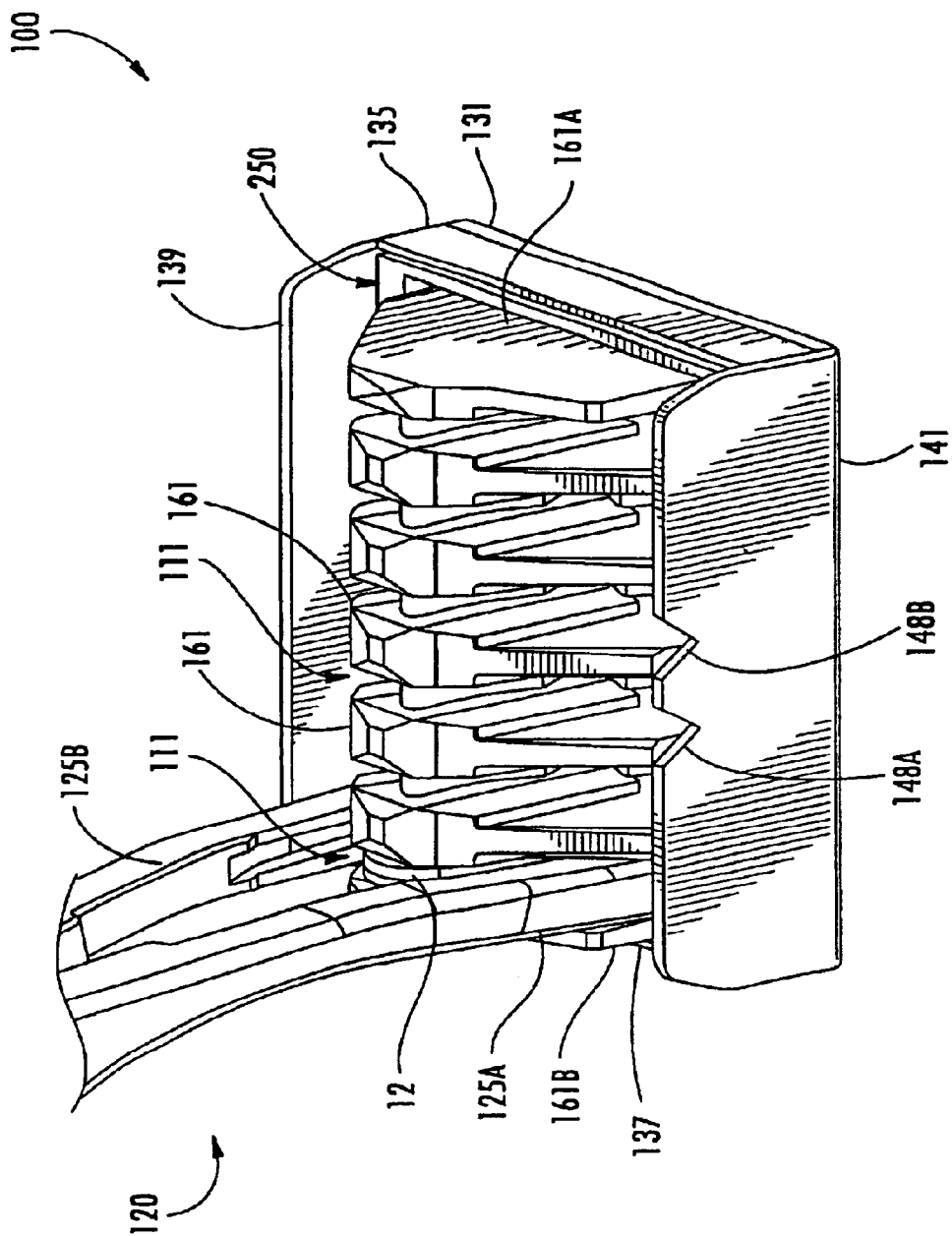
FIG. 2B is another perspective view of the clip cartridge, showing the clip applier engaging a clip loaded in one of the compartments of the clip cartridge.
Figure 2C:
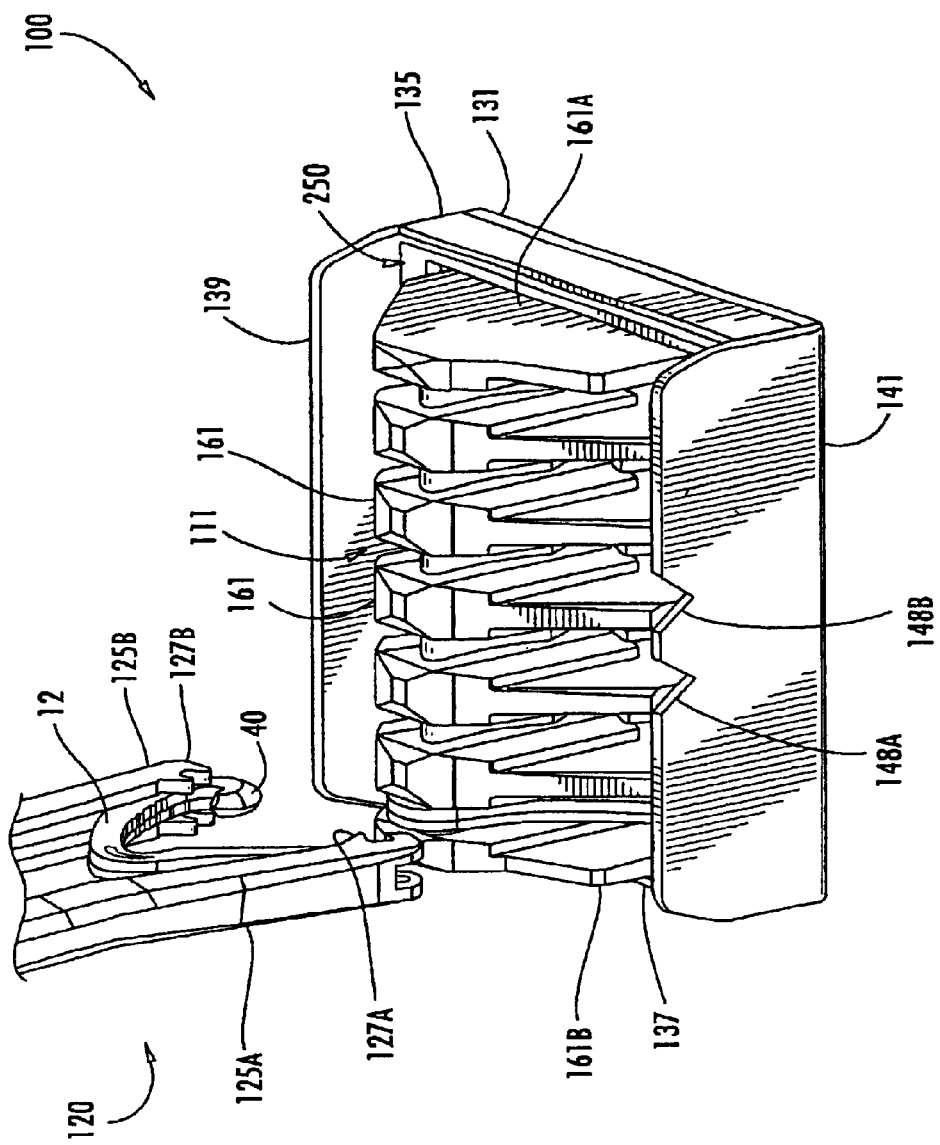
FIG. 2C is another perspective view of the clip cartridge, showing the clip being extracted from the compartment of the clip cartridge.
Figure 3:
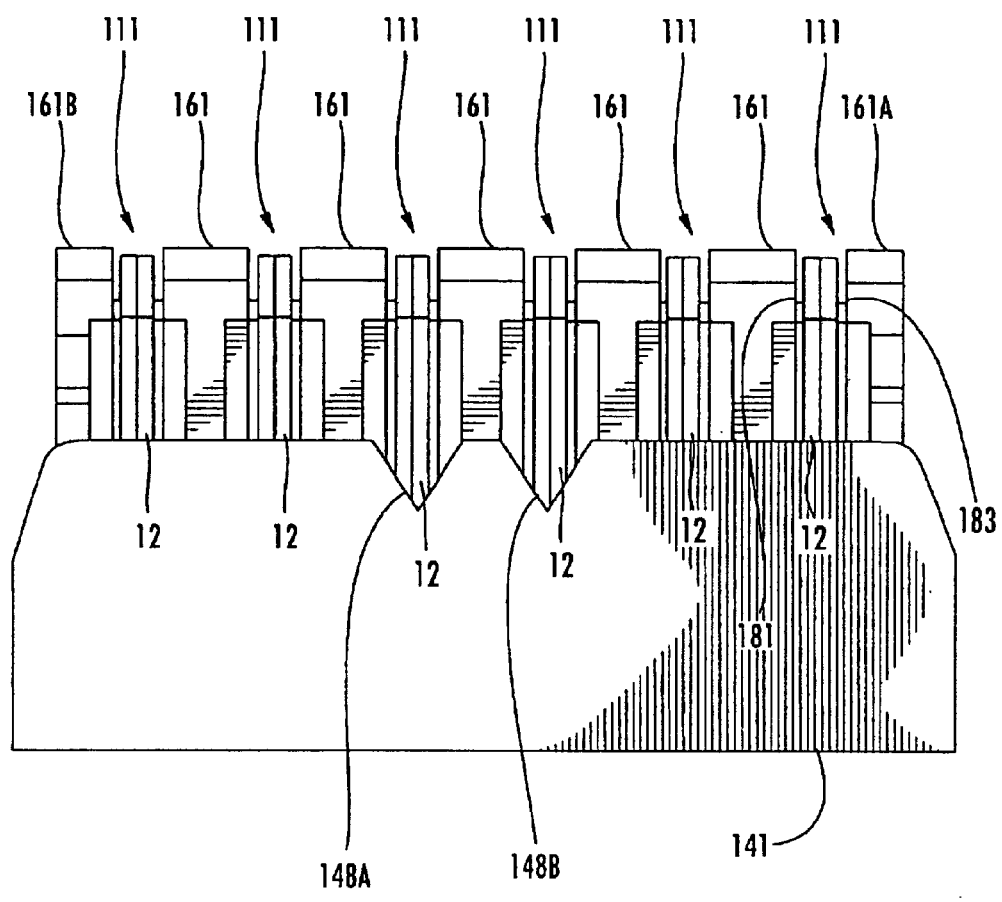
FIG. 3 is a side elevation view of the clip cartridge illustrated in FIGS. 2A–2C with several clips loaded therein.

Referring now to FIGS. 2A–2C, a preferred embodiment of a clip cartridge, generally designated 100, is provided in accordance with the present invention. Clip cartridge 100 preferably is constructed from a single-molded plastic body from which several features are formed. In particular, clip cartridge 100 comprises a plurality of clip retaining chambers or compartments 111 spaced along a longitudinal axis L of clip cartridge 100. Each clip compartment 111 is substantially identical and adapted for storing one clip 12, which preferably has an asymmetric design as described above and illustrated in FIGS. 1A and 1B. FIG. 2A illustrates one clip 12 in a stored condition in one of clip compartments 111. It will be understood, however, that preferred embodiments of clip cartridge 100 include several clip compartments 111 for storing several clips 12. As shown in FIG. 3, for instance, clip cartridge 100 of the present embodiment is adapted for storing six clips 12, although other embodiments can be provided that store more or less clips 12. If desired, an adhesive backing (not shown) can be provided on the underside of clip cartridge 100 to facilitate securing clip cartridge 100 to a tray or other supporting component during use.

FIGS. 2A–2C also illustrate the distal end of a representative clip applying instrument, generally designated 120, comprising opposing pivotable jaws 125A and 125B. Jaws 125A and 125B have respective jaw recesses 127A and 127B adapted to engage and retain bosses 56, 58, 62 and 64 of clip 12 (see FIGS. 1A and 1B). According to a method provided by the invention, FIG. 2A illustrates clip applying instrument 120 in a position over clip 12 prior to inserting clip applying instrument 120 into a selected clip compartment 111. FIG. 2B illustrates clip applying instrument 120 being inserted into selected clip compartment 111 to load clip 12 into locking engagement with clip applying instrument 120 (with bosses 56, 58, 62 and 64 retained in jaw recesses 127A and 127B). FIG. 2C illustrates the subsequent step of extracting clip 12 from clip cartridge 100 by removing clip applying instrument 120 with clip 12 loaded therein. This method is further described below with additional reference made to FIGS. 11A–11B.

Figure 4:
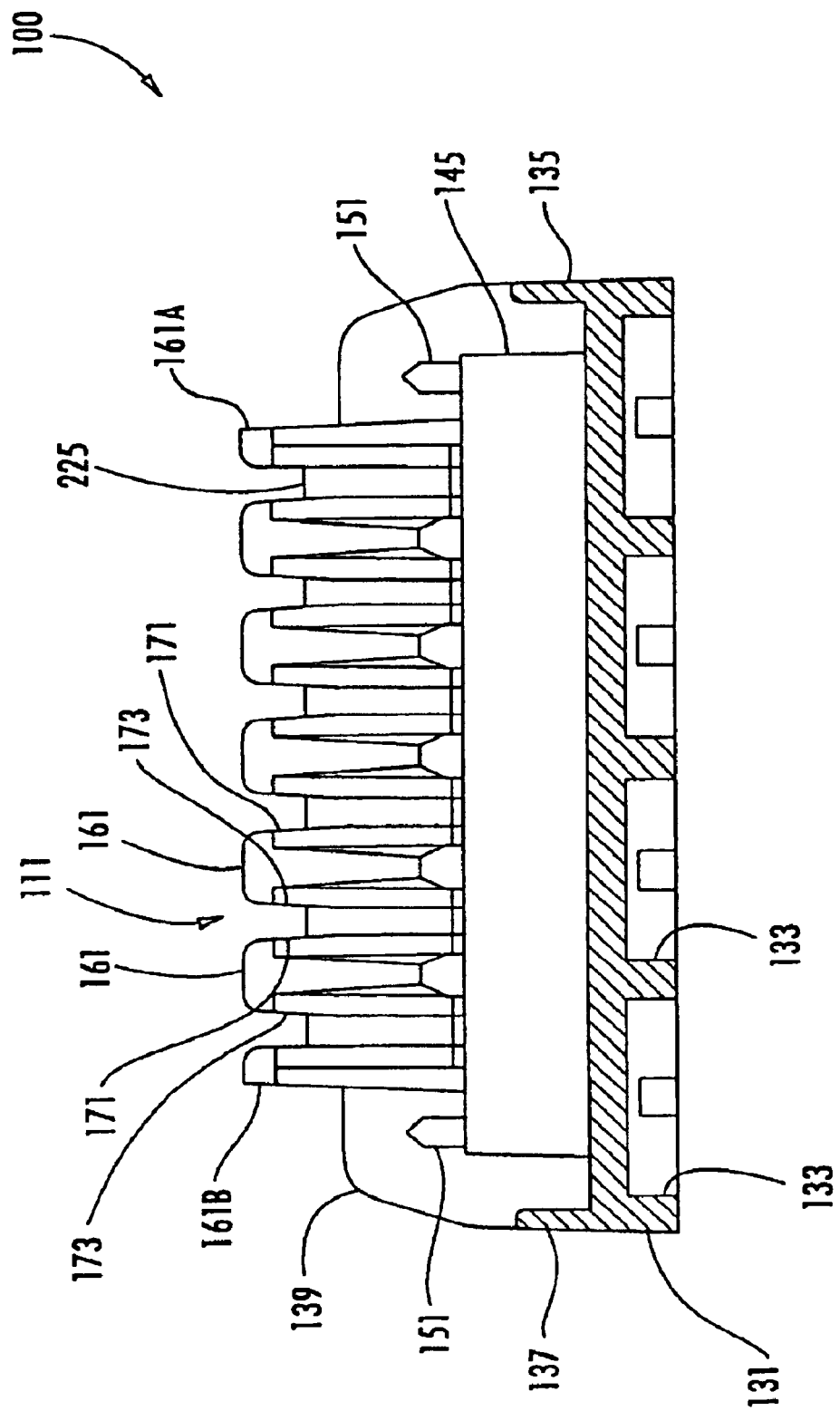
FIG. 4 is a side elevation view in partial cross section of the clip cartridge illustrated in FIGS. 2A–2C.
Figure 5:
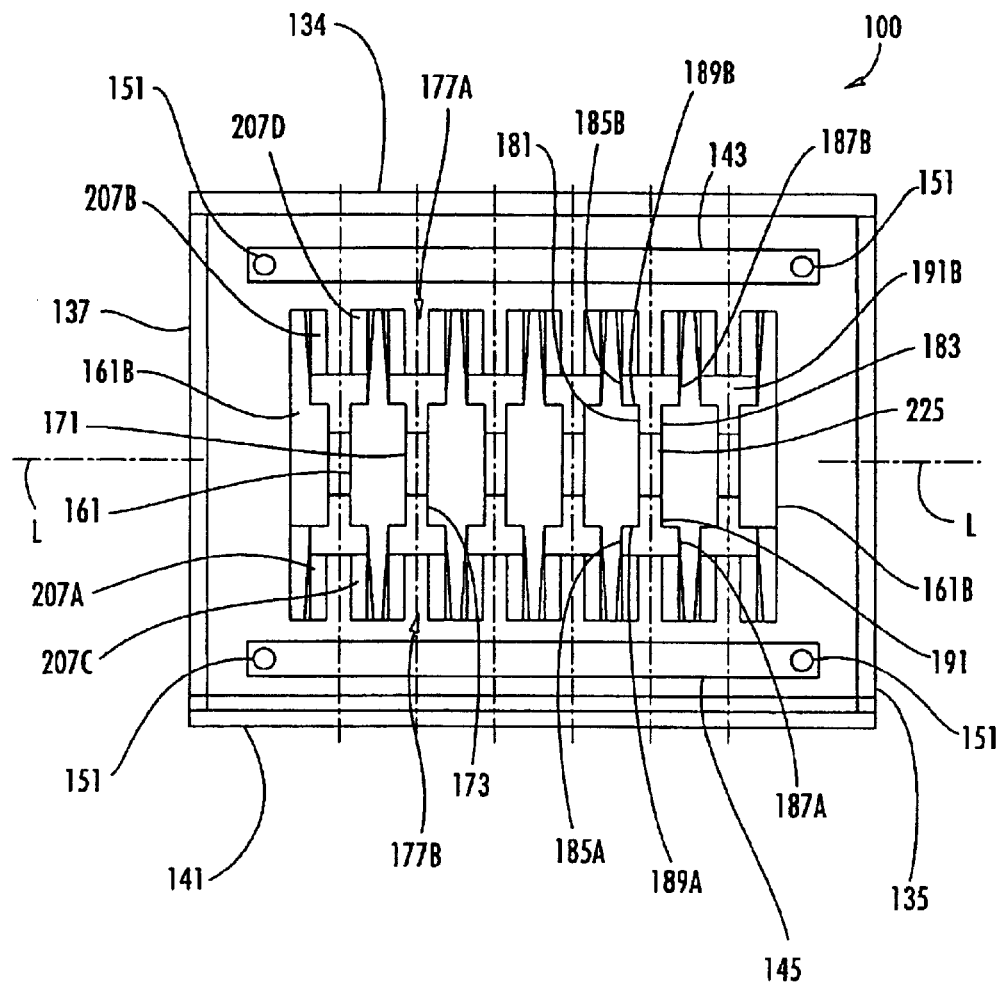
FIG. 5 is a top plan view of the clip cartridge illustrated in FIGS. 2A–2C.
Figure 8:
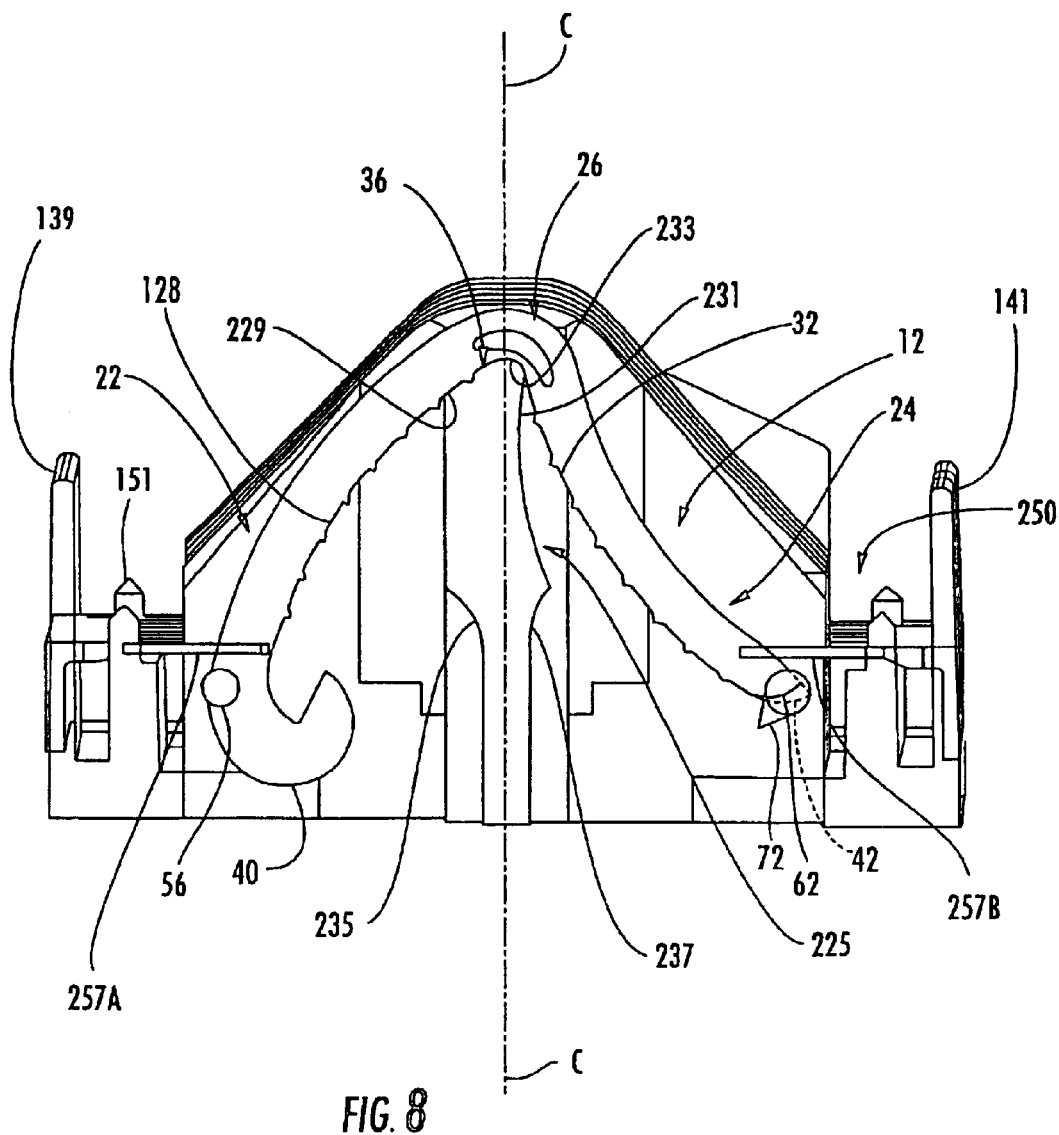
FIG. 8 is a perspective cross-sectional view of the clip cartridge illustrating a clip loaded in a clip compartment thereof.

Referring to FIGS. 2A and 4, clip cartridge 100 comprises a base portion 131. As shown in FIG. 4, base recesses 133 are formed in base portion 131 during the fabrication of clip cartridge 100 to reduce the amount of structural material needed. First and second axial end walls 135 and 137, first and second outer side walls 139 and 141 (see FIG. 2A), and first and second inner side walls 143 and 145 (see FIG. 5) extend upwardly from the perimeter of base portion 131. As will become evident from the description below, clip cartridge 100 is structured to enable asymmetric clips 12 to be loaded in only one orientation, with all clips 12 being loaded in that same orientation. Accordingly, as shown in FIGS. 2A and 8, the hook side of each clip 12 (containing first leg 22 as also shown in FIG. 1A) will always be stored on the side of clip cartridge 100 associated with first outer side wall 139, and the double-tooth side of each clip 12 (containing second leg 24 as also shown in FIG. 1A) will always be stored on the side of clip cartridge 100 associated with second outer side wall 141. As best shown in FIGS. 2A and 3, a pair of pointed notches 148A and 148B are cut into second outer side wall 141 to conveniently indicate to the user the orientation of clips 12 in clip cartridge 100. This indication facilitates the positioning of clip applying instrument 120 by the user during loading of clip 12 into jaws 125A and 125B of clip applying instrument 120 and subsequent extraction of clip 12 from clip cartridge 100. As shown in FIGS. 4 and 5, posts 151 are formed upwardly from the axial ends of each inner side wall 143 and 145 to facilitate the mounting of a clip retainer element to be described below.

Figure 6:
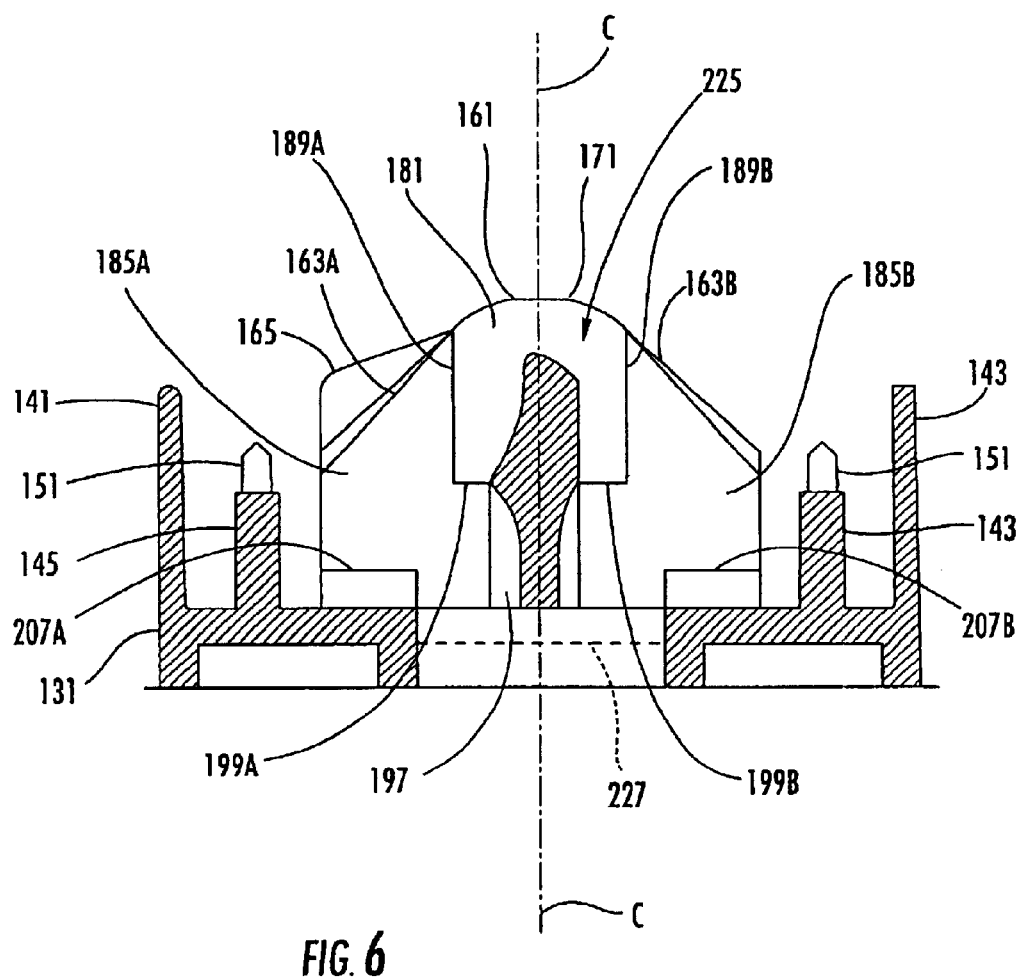
FIG. 6 is a cross-sectional view through the transverse width of the clip cartridge illustrated in FIGS. 2A–2C.
Figure 7:
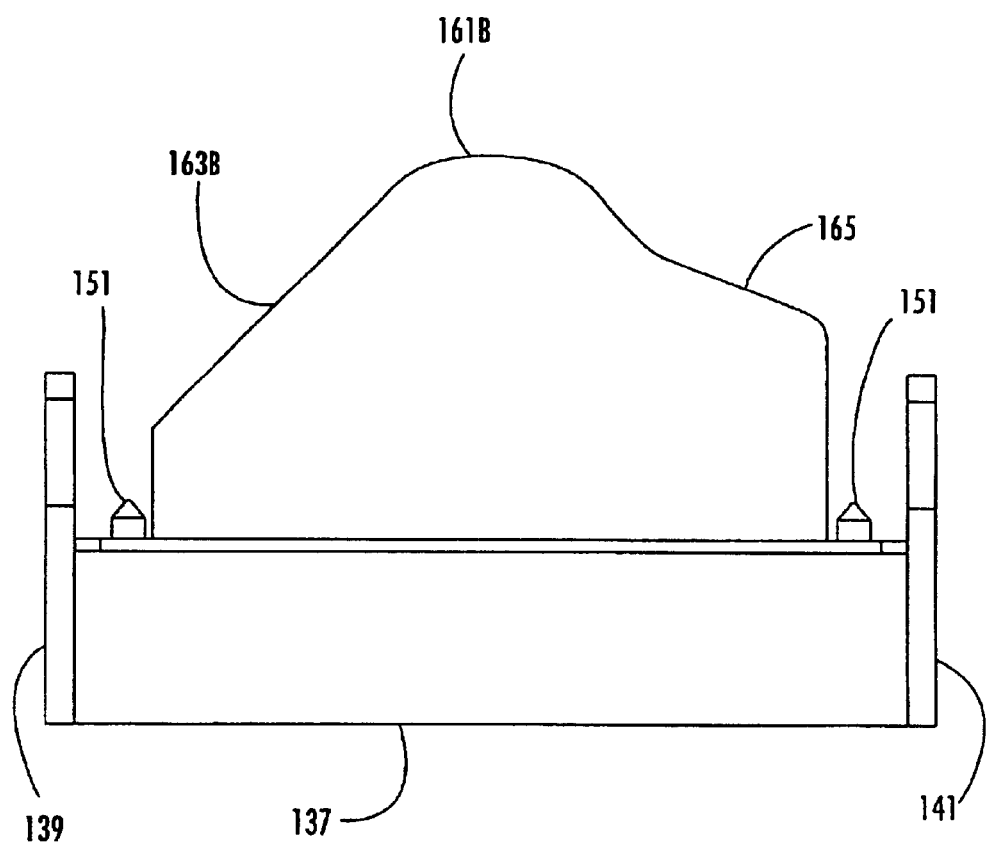
FIG. 7 is an end elevation view of the clip cartridge illustrated in FIGS. 2A–2C.

Referring to FIGS. 2A, 4 and 5, a plurality of transverse clip compartment walls 161 extend upwardly from base portion 131 and are spaced along longitudinal axis L of clip cartridge 100. The two transverse walls nearest to the axial ends of clip cartridge 100 (i.e., the first and seventh transverse walls in the specific example illustrated), are designated as outermost transverse walls 161A and 161B, respectively. Each pair of adjacent transverse walls 161 (including outermost transverse walls 161A and 161B) define a respective clip compartment 111 therebetween. As shown in FIG. 6, each transverse wall 161 is substantially symmetrical about a central wall axis C thereof. The upper section of each transverse wall 161 has tapered sections 163A and 163B on either side of central wall axis C to reduce cartridge mass and improve the accessibility of clips 12. As shown in FIGS. 2A and 7, as an alternative feature of the present embodiment, outermost transverse wall 161A (FIG. 2A) and outermost transverse wall 161B (FIG. 7) each include at least one tapered section 165 that is dissimilarly angled from the other corresponding tapered section 163B. Like the pair of pointed notches 148A and 148B formed in second outer side wall 141 of clip cartridge 100, dissimilar tapered sections 165 indicate to the user the orientation of clips 12 in clip cartridge 100, i.e., that clips 12 are oriented in clip cartridge 100 such that their double-tooth sides are disposed on the same side of longitudinal axis L as dissimilar tapered sections 165 of outermost transverse walls 161A and 161B.

Referring to FIGS. 4 and 5, each transverse wall 161 comprises a pair of oppositely facing transverse wall surfaces 171 and 173 that provide the axial boundaries of each compartment 111. For simplicity, wall surfaces facing to the left in FIGS. 4 and 5 are identified as 171 and those facing to the right are identified as 173. To define a given clip compartment 111, left wall surface 171 of one transverse wall 161 faces inwardly into clip compartment 111 from the left axial direction, and right wall surface 173 of an adjacent transverse wall 161 faces inwardly into the same clip compartment 111 from the opposite, right direction. From the perspective of FIG. 5, it can be seen that the oppositely facing transverse wall surfaces 171 and 173 associated with each clip compartment 111 define a pair of oppositely facing lateral openings, generally designated 177A and 177B, respectively, into clip compartment 111 on either side of longitudinal axis L of clip cartridge 100. As described below, portions of a clip retaining element extend into each clip compartment 111 through these lateral openings 177A and 177B.

One of left wall surfaces 171 is shown in detail in FIG. 6, although it will be understood that the features of each left wall surface 171 have symmetrical counterparts on each right wall surface 173 as shown in FIG. 5. Left wall surface 171 includes a main left wall portion 181 that is spaced across clip compartment 111 from a main right wall portion 183 of its oppositely facing right wall surface 173. Preferably, this spacing is an amount slightly greater than the width of the body of clip 12 to be received in clip compartment 111 as shown, for example, in FIG. 3. Left wall surface 171 further includes recessed left wall portions 185A and 185B substantially symmetrically arranged on either side of main left wall portion 181. As shown in FIG. 5, each right wall surface 173 likewise includes symmetrically arranged recessed right wall portions 187A and 187B facing corresponding recessed left wall portions 185A and 185B. The distance between each corresponding pair of oppositely facing recessed left and right wall portions 185A/187A and 185B/187B is greater than the spacing between oppositely facing main left and right wall portions 181 and 183. The difference in these spacings accommodates bosses 56, 58, 62 and 64 of clip 12 (see FIG. 1B) and improves access by jaws 125A and 125B of clip applying instrument 120 (see FIGS. 2A–2C), while limiting any twisting of clips 12 in their respective clip compartments 111. As shown in FIGS. 5 and 6, the spacings also create vertically extending ledges 189A, 189B, 191A and 191B perpendicular to respective wall portions 185A, 185B, 187A and 187B, which serve as guides to center clip applying instrument 120 as it is inserted into one of clip compartments 111, thereby ensuring proper loading of clip 12 into jaws 125A and 125B of clip applying instrument 120.

It can be further seen in FIG. 6 that each main left wall portion 181 has a reduced-width section 197 defining shoulders 199A and 199B on either side of central wall axis C, at the interface between main left wall portion 181 and respective recessed left wall portions 185A and 185B. For each clip compartment 111, it will be understood that main right wall portion 183 has a similar reduced-width section and shoulders that face reduced-width section 197 and shoulders 199A and 199B of corresponding main left wall portion 181. These features create wider open areas in the lower section of each clip compartment 111 on either side of central wall axis C. This configuration facilitates the proper loading of clip 12 into jaws 125A and 125B of clip applying instrument 120 (see FIGS. 2A–2C) by providing additional clearance through which the distal ends of clip 12 can deflect in response to contact with jaws 125A and 125B. The configuration also enables additional free play in the distal ends of jaws 125A and 125B while the user manipulates clip applying instrument 120 into proper engagement with clip 12, as described in more detail below. Preferably, recessed wall portions 185A, 185B, 187A and 187B do not extend entirely across the width of the body of clip 12 or to the bottom of clip compartment 111. Instead, as shown in FIGS. 5 and 6, clip cartridge 100 comprises bottom ledges 207A, 207B, 207C and 207D disposed in each clip compartment 111 on either side of longitudinal axis L of clip cartridge 100, and which are generally parallel to the upper surfaces of base portion 131. Bottom ledges 207A, 207B, 207C and 207D serve as stops to provide a lower limit on the excursion of clip applying instrument 120 into each clip compartment 111.

Referring now to FIGS. 4–6 and 8, each clip compartment 111 of clip cartridge 100 includes a clip supporting element 225 in the form of a saddle or post. As shown in FIGS. 4 and 5, in each clip compartment 111, clip supporting element 225 is preferably joined between corresponding main left and right wall portions 181 and 183. As shown in FIG. 6, each clip support element 225 also preferably extends from a central section 227 of base portion 131. As alternatives, clip support element 225 could be joined between main left and right wall portions 181 and 183 without being supported by base portion 131, or could be supported by base portion 131 without being joined with main left and/or right wall portions 181 and 183. As shown in FIGS. 6 and 8, the cross-section of clip supporting element 225 extends outwardly on either side of central wall axis C, but is asymmetrically shaped such that at least its upper region conforms to the asymmetric shape of clip 12. More specifically, referring to FIG. 8, clip supporting element 225 includes a convex support edge 229, a concave support edge 231, and a rounded top support edge 233 that joins convex support edge 229 and concave support edge 231. Preferably, rounded top support edge 233 is disposed in an offset relation to central wall axis C, with its apex located to one side of central wall axis C, as illustrated in FIGS. 6 and 8.

As shown in FIG. 8, the contour of clip supporting element 225 enables clip 12 to be snugly supported thereon. In the fully seated position of clip 12 on clip supporting element 225, concave inner surface 36 of hinge section 26 of clip 12 conformally contacts and is supported by rounded top support edge 233 of clip supporting element 225. A portion of concave inner surface 28 of first leg 22 of clip 12 conformally contacts and is supported by convex support edge 229 of clip supporting element 225. It can also be seen that if clip 12 attempts to rock or pivot in the clockwise direction (from the perspective of FIG. 8), convex inner surface 32 of second leg 24 will conformally contact concave support edge 231 of clip supporting element 225, thereby restricting lateral or transverse movement of clip 12 on rounded top support edge 233.

In comparison to the upper region of the cross-section of clip supporting element 225, the lower region has a reduced cross-section defined by lower concave edges 235 and 237 on either side of central wall axis C. This reduced cross-section provides clearance for movement of jaws 125A and 125B of clip applying instrument 120 and for defection of first and second legs 22 and 24 of clip 12 during insertion of jaws 125A and 125B into clip compartment 111 and subsequent removal of clip 12 and jaws 125A and 125B therefrom.

The asymmetric configuration of clip supporting element 225 significantly reduces the freedom accorded to clip 12 for rocking on or otherwise moving in relation to clip supporting element 225, thereby facilitating engagement of clip 12 by clip applying instrument 120 (see FIGS. 2A–2C). At the same time however, first and second legs 22 and 24 of clip 12 are free to deflect in response to contact by clip applying instrument 120, and in response to the resulting downward force imparted to first and second legs 22 and 24 by clip applying instrument 120, as clip applying instrument 120 is inserted into clip compartment 111. This ensures that respective bosses 56, 58, 62 and 64 of clip 12 move around the outer edges of jaws 125A and 125B of clip applying instrument 120 and into eventual engagement with jaw recesses 127A and 127B. Moreover, the asymmetric configuration of clip supporting element 225 maintains clip 12 in a proper position thereon such that jaw recesses 127A and 127B engage each boss 56, 58, 62 and 64 simultaneously or substantially simultaneously, which further facilitates engagement of clip 12 by clip applying instrument 225.

Figure 9:
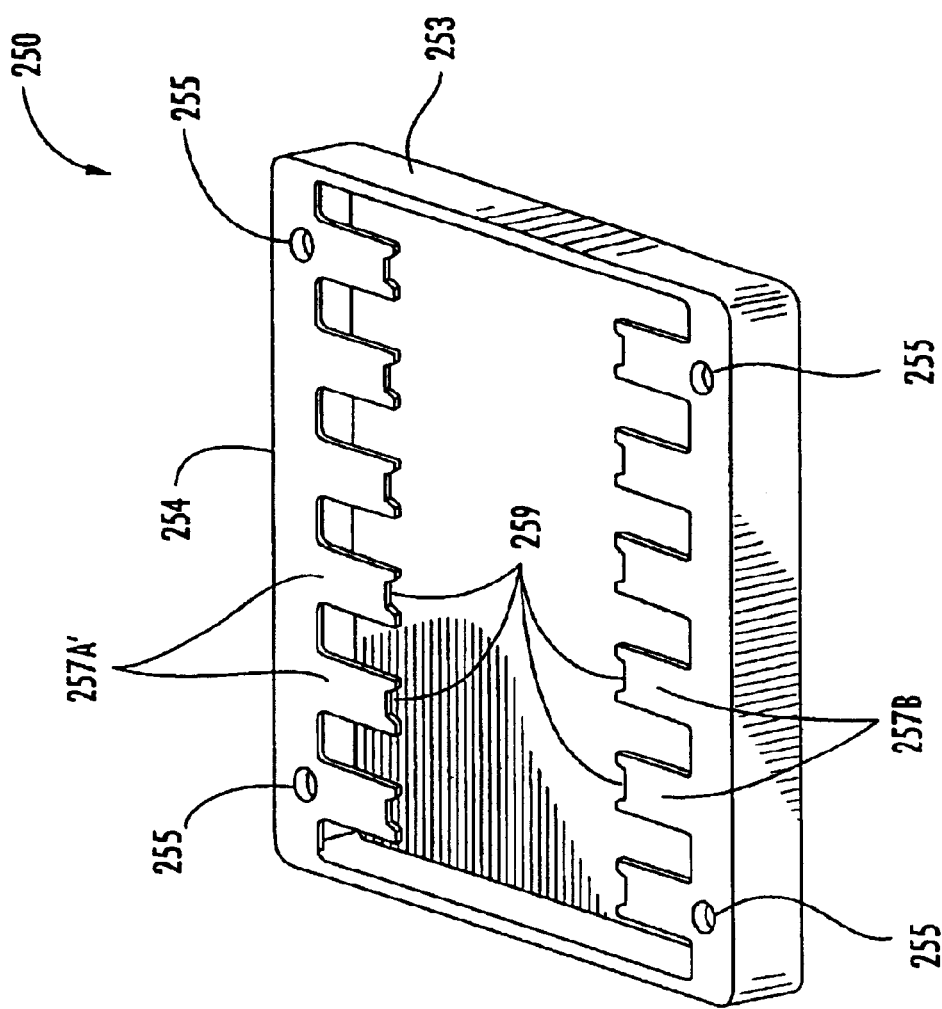
FIG. 9 is a perspective view of a clip retaining element provided with the clip cartridge in accordance with the present invention.
Figure 10:
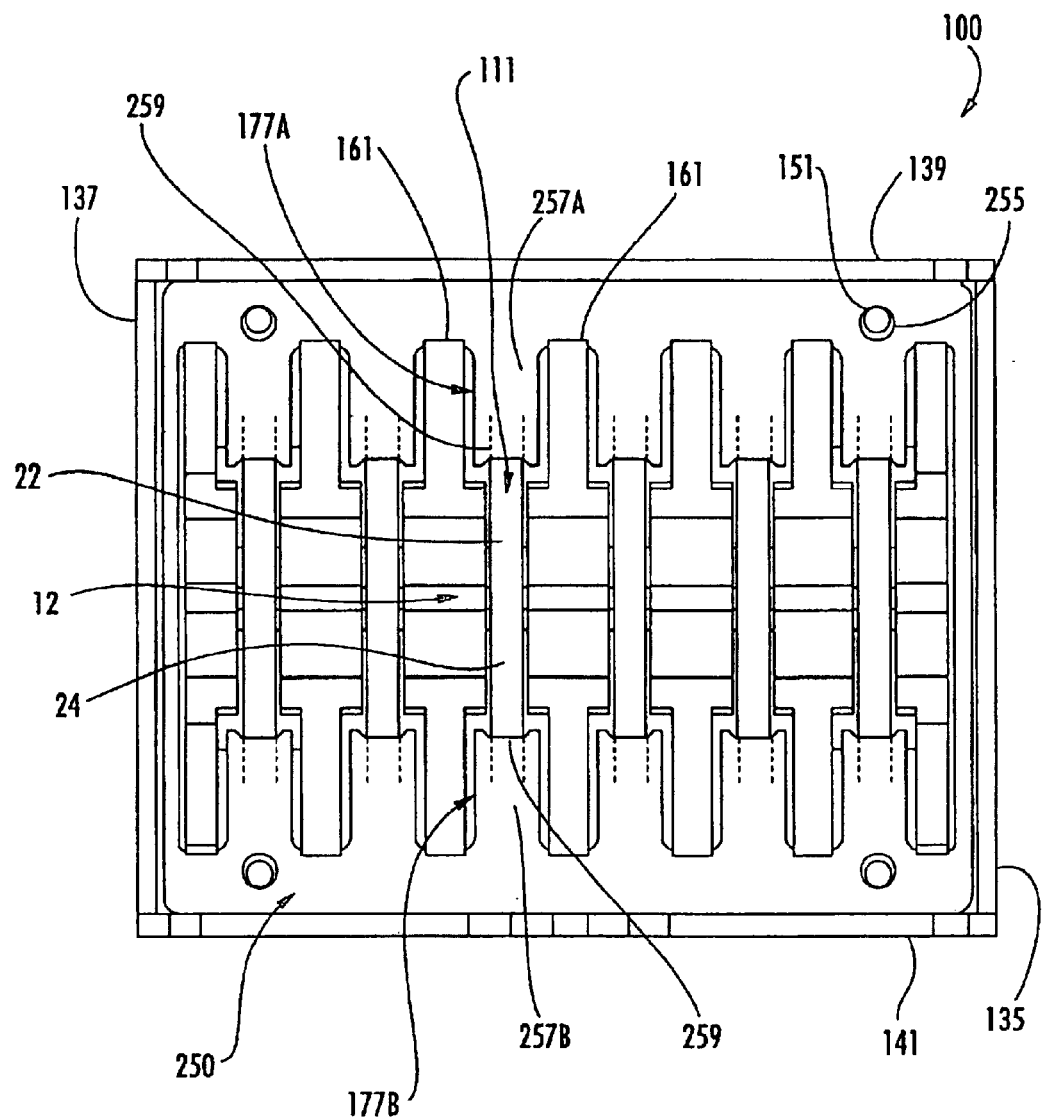
FIG. 10 is a top plan view of the clip cartridge illustrated in FIGS. 2A–2C with the clip retaining element illustrated in FIG. 9 mounted therein.

Referring now to FIGS. 9 and 10, clip cartridge 100 further comprises a clip retainer element, generally designated 250. Clip retainer element 250 is preferably constructed from a resilient material such as polyethylene, which even more preferably is also clear or translucent. Clip retainer element 250 generally includes a box-like outer frame structure 253. An aperture 255 is preferably formed at each corner of a top surface 254 of frame structure 253. A series of opposing pairs of resilient fingers or tabs 257A and 257B extend inwardly from top surface 254 toward each other, with each pair of tabs 257A and 257B being axially spaced from adjacent pairs of tabs 257A and 257B. Preferably, each tab 257A and 257B terminates at an inner edge having a tab recess 259. As shown in FIG. 10, once clips 12 have been loaded into respective clip compartments 111 prior to sealing and packaging clip cartridge 100, clip retainer element 250 is mounted into the confines of clip cartridge 100. To secure clip retainer element 250 in clip cartridge 100, each aperture 255 is fitted onto each corresponding post 151 of each inner side wall 143 and 145 (see FIG. 5) of clip cartridge 100. In the mounted position of clip retaining element 250, each tab 257A and 257B extends into each clip compartment 111 from a corresponding lateral opening 177A and 177B thereof and its tab recess 259 contacts a respective first or second leg 22 or 24 of clip 12. As evident from FIG. 8, bosses 56, 58, 62 and 64 of each clip 12 are housed below each corresponding tab 257A and 257B. In this manner, clips 12 are prevented from undue movement within clip compartments 111, which is primarily important during handling and shipping of a packaged clip cartridge 100.

Figure 11A:
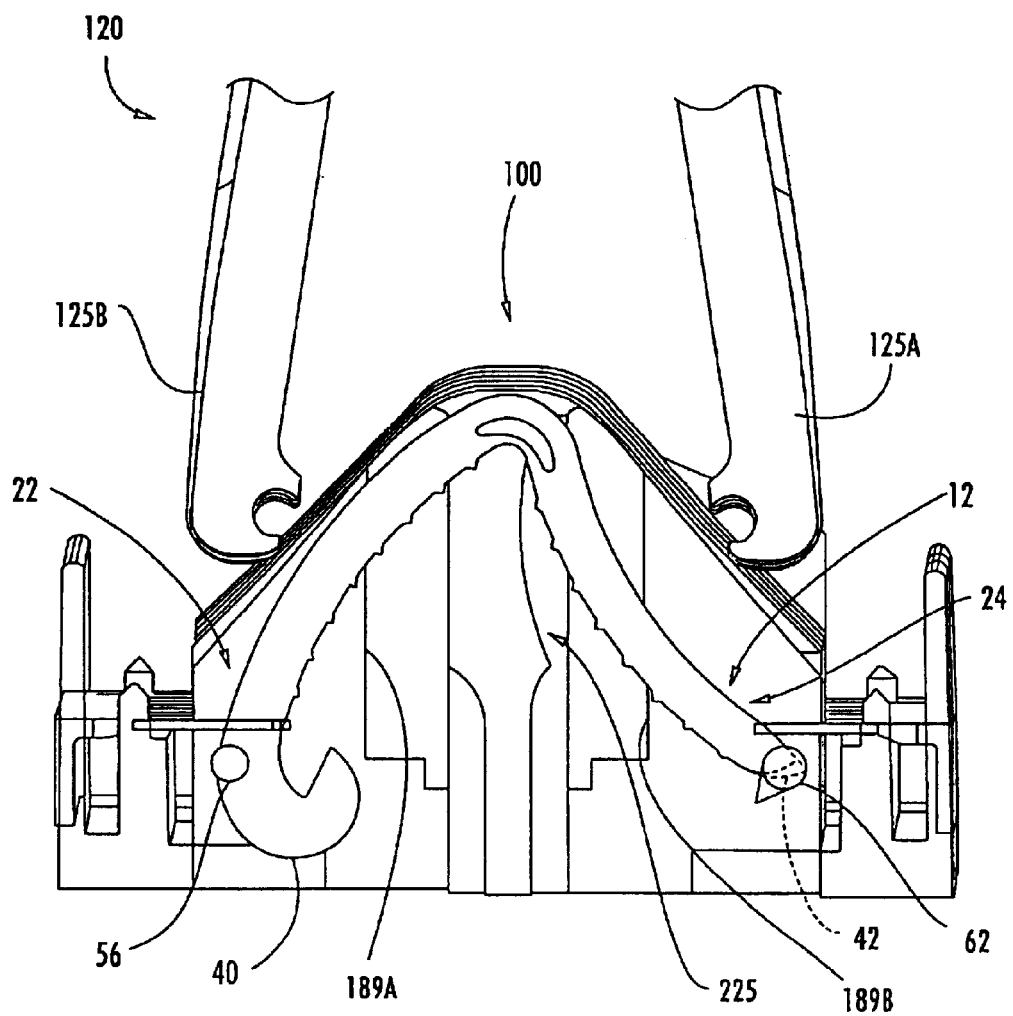
FIG. 11A is a cross-sectional view of the clip cartridge showing a clip applier being inserted into a compartment thereof.
Figure 11B:
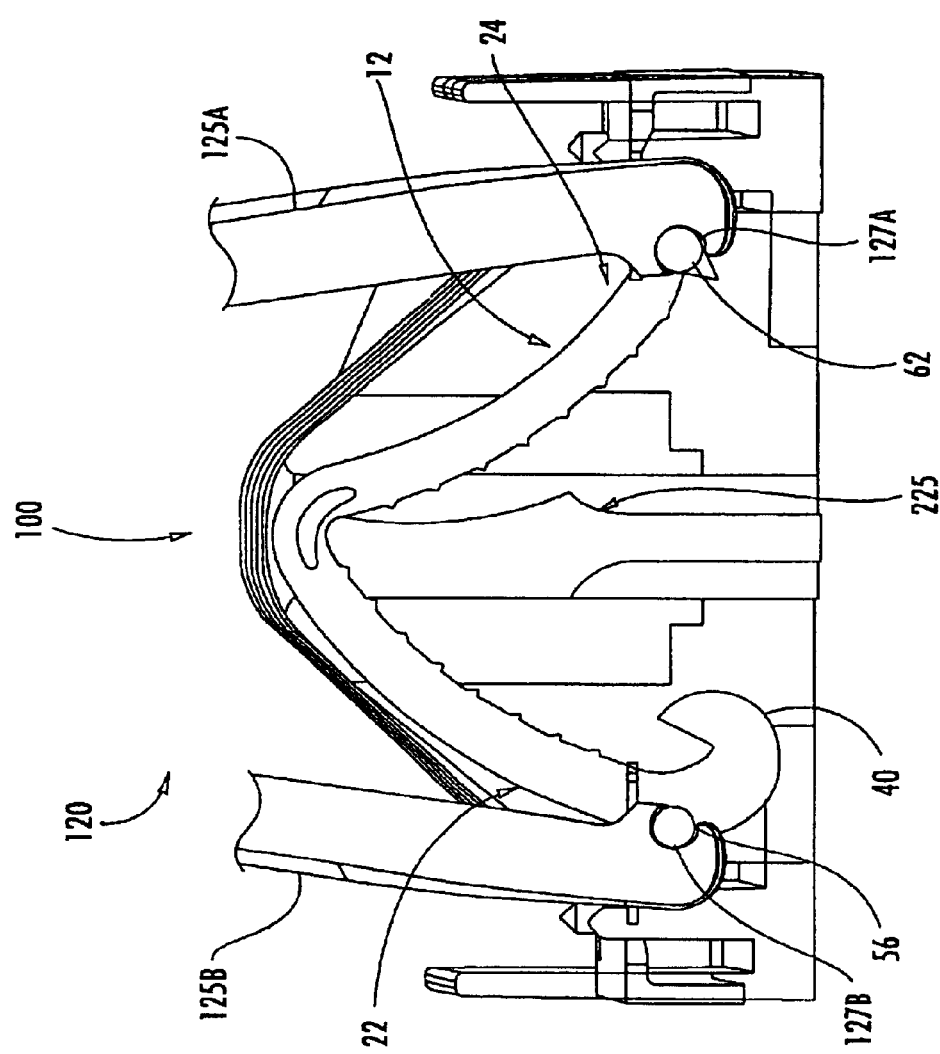
FIG. 11B is a cross-sectional view of the clip cartridge showing the clip applier engaging a clip loaded in one of the compartments of the clip cartridge.

Referring now to FIGS. 11A–11C as well as FIGS. 2A–2C, a method by which clips 12 can be extracted from clip cartridge 100 will now be described. FIGS. 2A and 11A show jaws 125B and 125B of clip applier 120 being inserted into a selected clip compartment 111. Referring specifically to FIG. 11A, vertical ledges 189A and 189B (as well as opposing vertical ledges 191A and 191B shown in FIG. 5) prevent jaws 125A and 125B from unduly compressing first and second legs 22 and 24 of clip 12, and hence assist in properly guiding jaws 125A and 125B toward hook section 40 and tip section 42 of clip 12 and into contact with bosses 56, 58, 62 and 64. Continued downward insertion of jaws 125A and 125B into clip compartment 111 causes the distal ends of jaws 125A and 125B to contact bosses 56, 58, 62 and 64. The downward movement of jaws 125A and 125B and their contact with bosses 56, 58, 62 and 64 in effect cause the distal ends of jaws 125A and 125B to act as cam surfaces. As a result, hook section 40 and tip section 42 of clip 12 deflect inwardly toward central wall axis C, and bosses 56, 58, 62 and 64 move around the distal ends of jaws 125A and 125B until they are forced into seating engagement within respective jaw recesses 127A and 127B as shown in FIGS. 2B and 11B. It will be noted that while hook section 40 and tip section 42 are free to move in this manner, and further that the distal regions of first and second legs 22 and 24 are necessarily deflected as well, the asymmetric configuration of clip supporting element 225 nonetheless retains clip 12 in its properly seated position. Hence, clip supporting element 225 as designed according to the invention prevents misalignment of jaws 125A and 125B with clip 12 during insertion into clip compartment 111 and engagement with clip 12. In addition, the design of clip supporting element 225 enables bosses 56, 58, 62 and 64 to engage respective jaw recesses 127A and 127B with sufficient force as to produce an audible click, which indicates to the user that clip 12 has been successfully loaded into jaws 125A and 125B. Finally, as shown in FIGS. 2C and 11C, once jaws 125A and 125B have successfully engaged clip 12, jaws 125A and 125B are pulled out of clip compartment 111 with clip 12 fully engaged therein, allowing clip 12 to be removed from clip cartridge 100 in preparation for use in a desired surgical procedure.

It will be understood that various details of the invention may be changed without departing from the scope of the invention. Furthermore, the foregoing description is for the purpose of illustration only, and not for the purpose of limitation—the invention being defined by the claims.

What is claimed is:

1. A cartridge for retaining surgical clips, comprising:
   (a) a base having a base longitudinal axis;
   (b) a plurality of axially spaced walls extending from the base and transversely disposed in relation to the base axis, the walls defining a plurality of axially spaced compartments therebetween; and
   (c) a plurality of clip support members, each clip support member disposed within a respective compartment and comprising a concave support edge, a convex support edge, and a rounded support edge joining the concave support edge and the convex support edge.

2. The cartridge according to claim 1 wherein each wall has a central wall axis, and each rounded support edge is disposed in an offset relation to the central wall axis.

3. The cartridge according to claim 1 comprising an asymmetric clip disposed in one of the compartments, the clip comprising a first leg, a second leg and a hinge region joining the first and second legs, wherein the hinge region is supported by the rounded support edge of the corresponding clip supporting member, the first leg is adapted for contacting the convex support edge, and the second leg is adapted for contacting the concave support edge.

4. The cartridge according to claim 1 wherein each compartment comprises first and second lateral openings, the first lateral opening is defined on a first side of the base axis between a corresponding adjacent pair of the walls, and the second lateral opening is defined on a second side of the base axis in opposing relation to the first lateral opening between the pair of walls.

5. The cartridge according to claim 4 comprising a clip retainer supported by the base and comprising a plurality of opposing pairs of first and second resilient tabs, each first tab extending into a corresponding compartment through its corresponding first lateral opening, and each second tab extending into the corresponding compartment through its corresponding second lateral opening.

6. The cartridge according to claim 5 wherein each first and second tab terminates at an inside tab edge, and each inside tab edge comprises a tab recess.

7. A cartridge for retaining surgical clips, comprising:
   (a) a base having a base longitudinal axis;
   (b) a plurality of axially spaced walls extending from the base and transversely disposed in relation to the base axis, the walls defining a plurality of axially spaced compartments therebetween, each wall having a central wall axis generally perpendicular to the base axis;
   (c) a plurality of clip support members, each clip support member disposed within a respective compartment and comprising arcuate side surfaces and a cross-section asymmetrically shaped in relation to the central wall axis; and
   (d) wherein said arcuate side surfaces comprises one arcuate side surface of each clip support member which is a convex support edge, another arcuate side surface of each clip support member which is a concave support edge and a rounded support edge joins the concave support edge and the convex support edge.

8. The cartridge according to claim 7 wherein each rounded support edge is disposed in an offset relation to the central wall axis.

9. A cartridge for retaining surgical clips, comprising:
   (a) a base having a base longitudinal axis;
   (b) a plurality of axially spaced walls extending from the base and transversely disposed in relation to the base axis, the walls defining a plurality of axially spaced compartments therebetween, each compartment comprising a first lateral opening defined on a first side of the base axis and a second lateral opening defined on a second side of the base axis in opposing relation to the first lateral opening;
   (c) a plurality of asymmetric clip support members, each clip support member disposed within a respective compartment above the base;
   (d) a clip retainer supported by the base and comprising a plurality of opposing pairs of first and second resilient tabs, each first tab extending into a corresponding compartment through its corresponding first lateral opening, and each second tab extending into the corresponding compartment through its corresponding second lateral opening;
   (e) wherein each wall has a central wall axis generally perpendicular to the base longitudinal axis, and each clip support member comprises arcuate support surfaces having an asymmetrically shaped cross-section in relation to the central wall axis; and
   (f) wherein each clip support member comprises a concave support edge, a convex support edge, and a rounded support edge joining the concave support edge and the convex support edge.

10. The cartridge according to claim 9 wherein each rounded support edge is disposed in an offset relation to the central wall axis.

* * * * *